(12) United States Patent
Venkateswarlu et al.

(10) Patent No.: US 7,388,024 B2
(45) Date of Patent: Jun. 17, 2008

(54) INDENO[2,1A]INDENES AND ISOINDOLO[2,1-A]INDOLES

(75) Inventors: Jasti Venkateswarlu, Andhra Pradesh (IN); Satya Nirogi Ramakrishna Venkata, Andhra Pradesh (IN); Sastri Kambhampati Rama, Andhra Pradesh (IN); Shreekrishna Shirsath Vikas, Andhra Pradesh (IN); Kandikere Vishwottam Nagaraj, Andhra Pradesh (IN)

(73) Assignee: Suven Life Sciences Limited, Hyderabad (IN)

( * ) Notice: Subject to any disclaimer, the term of this patent is extended or adjusted under 35 U.S.C. 154(b) by 0 days.

(21) Appl. No.: 11/478,968

(22) Filed: Jun. 29, 2006

(65) Prior Publication Data

US 2007/0054946 A1 Mar. 8, 2007

Related U.S. Application Data

(63) Continuation of application No. PCT/IN2004/000430, filed on Dec. 30, 2004.

(30) Foreign Application Priority Data

Jan. 2, 2004 (IN) .............................. 5/CHE/2004

(51) Int. Cl.
*C07D 403/04* (2006.01)
*C07D 513/04* (2006.01)
*A61K 31/401* (2006.01)
*A61K 31/425* (2006.01)
*A61K 49/00* (2006.01)

(52) U.S. Cl. .................. 514/373; 514/410; 534/10; 534/14; 548/420; 424/9.42; 424/9.44

(58) Field of Classification Search ............... 548/420; 534/10, 14; 424/9.42, 9.44; 514/373, 410
See application file for complete search history.

(56) References Cited

U.S. PATENT DOCUMENTS 7,297,711 B2 * 11/2007 Jasti et al. .................. 514/410
7,317,035 B2 * 1/2008 Jasti et al. .................. 514/410
2003/0191124 A1 10/2003 Merce-Vidal

FOREIGN PATENT DOCUMENTS

| WO | WO-02/051837 A2 | 7/2002 |
|---|---|---|
| WO | WO-03/035061 A1 | 5/2003 |
| WO | WO-03/053433 A1 | 7/2003 |
| WO | WO-03/065046 A2 | 8/2003 |
| WO | WO-03/066056 A1 | 8/2003 |
| WO | WO-2004/000205 A2 | 12/2003 |
| WO | WO-2004/000845 A1 | 12/2003 |
| WO | WO-2004/000849 A2 | 12/2003 |
| WO | WO-2004/048328 A2 | 6/2004 |
| WO | WO-2004/048330 A1 | 6/2004 |
| WO | WO-2004/048331 A1 | 6/2004 |
| WO | WO-2004/055026 A1 | 7/2004 |

OTHER PUBLICATIONS

Itahara, Toshio, Heterocycles, 24(9), 2557-2562, 1986.*
"PCT Application No. PCT/IN2004/000430, International Search Report mailed Jun. 24, 2005", 4 pgs.

* cited by examiner

*Primary Examiner*—Fiona T Powers
(74) *Attorney, Agent, or Firm*—Schwegman, Lundberg & Woessner P.A.

(57) ABSTRACT

The present invention provides indeno[2,1a]indene and isoindolo[2,1-a]indole derivatives of the Formula I, its salts and its stereoisomers, wherein X, $R_1$, $R_2$, $R_3$, $R_4$, $R_6$, $R_7$, $R_8$, $R_9$, $R_{11}$, $R_{12}$, $R_{13}$ and $R_{14}$ are as described in the specification.

Formula (I)

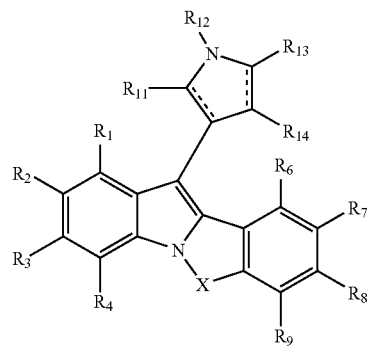

The invention also provides a method to prepare the compound of formula I, pharmaceutical composition containing such compounds, and method to manufacture a medicament. These compounds are useful in the treatment of various CNS disorders, hematological disorders, eating disorders, diseases associated with pain, respiratory diseases, genitourological disorders, cardio vascular diseases and cancer.

10 Claims, No Drawings

INDENO[2,1A]INDENES AND ISOINDOLO[2,1-A]INDOLES

RELATED APPLICATION

This application is a continuation under 35 U.S.C. 111(a) of PCT/IN2004/000430, filed on Dec. 30, 2004 and published on Jul. 21, 2005 as WO 2005/066184 A1, which claims priority under 35 U.S.C. 119 from Indian Application No. 5/CHE/2004, filed Jan. 2, 2004, which applications are incorporated herein by reference in their entirety.

FIELD OF THE INVENTION

The present invention relates to a compound of the general formula (I):

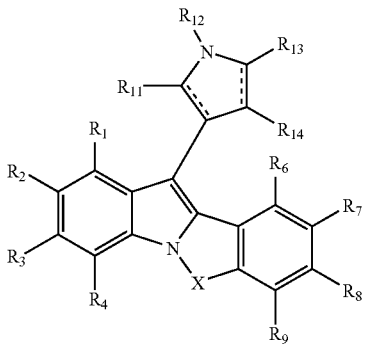

Formula (I)

SUMMARY OF THE INVENTION

It is one of the important objects of the present invention to provide a compound of the Formula (I) or a pharmaceutically acceptable salt, a stereoisomer/s thereof:

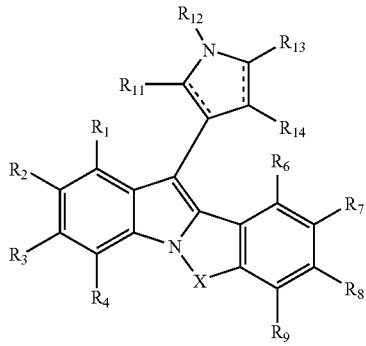

(I)

wherein X can be —$CH_2$—, —CO—, —S—, —S(O) or —$S(O)_2$;

[===] represents either a single or a double bond;

$R_1$, $R_2$, $R_3$, $R_4$, $R_6$, $R_7$, $R_8$ and $R_9$ each independently represent hydrogen, halogen, perhaloalkyl, perhaloalkoxy, hydroxy, ($C_1$-$C_3$)alkyl, ($C_3$-$C_5$)cycloalkyl, ($C_1$-$C_3$)alkoxy, cyclo($C_3$-$C_5$)alkoxy, aryl, aryloxy, aralkyl, aralkoxy, heterocyclyl, monoalkylamino, dialkylamino or thioalkyl;

$R_{11}$, $R_{12}$, $R_{13}$ and $R_{14}$, each independently represent hydrogen, halogen, oxo, thio, perhaloalkyl, perhaloalkoxy, hydroxy, thiol or ($C_1$-$C_3$)alkyl.

Another object of the present invention is to provide a compounds of the formula (I) which could be agonists, partial agonist or antagonists at the 5-ht receptor sub-types.

Accordingly, the present invention provides indeno[2,1a] indene and isoindolo[2,1-a]indole derivatives of the Formula (I), its salts and its stereoisomers, wherein X, $R_1$, $R_2$, $R_3$, $R_4$, $R_6$, $R_7$, $R_8$, $R_9$, $R_{11}$, $R_{12}$, $R_{13}$ and $R_{14}$ are as described above.

The invention also provides a method to prepare compound with formula (I), pharmaceutical composition containing such compounds and method to manufacture a medicament. These compounds are useful in the treatment of various CNS disorders, hematological disorders, eating disorders, diseases associated with pain, respiratory diseases, genito-urological disorders, cardio vascular diseases and cancer.

DETAILED DESCRIPTION OF THE INVENTION

Compounds of formula (I) are useful in treating various disorders that involve 5-HT receptors (Serotonin) (International Patent Publication WO 03/065046 A2), preferably those having discriminatory profile and strong affinity towards the particular receptor. Mediation of 5-$ht_6$ receptors has been proposed for treating various CNS disorders, hematological disorders, eating disorders, diseases associated with pain, respiratory diseases, genito-urological disorders, cardio vascular diseases and cancer.

These compounds can be formulated into various dosage forms, whereby an effective amount could be delivered to the patient in need, either to obtain a therapeutic or diagnostic benefit. International Patent Publications WO 2004/000205, WO 2004/000845, WO 2004/000849, WO 2004/055026 A1, WO 2004/048331 A1, WO 2004/048330 A1 and WO 2004/048328 A2 (all assigned to Suven Life Sciences Limited) describe various compounds and treatment methods. These PCT applications and the references reported therein are all incorporated herein.

International Patent Publication WO 03/066056 A1 reports that antagonism of 5-$HT_6$ receptor could promote neuronal growth within the central nervous system of a mammal. Another International Patent Publication WO 03/065046 A2 discloses new variant of human 5-$HT_6$ receptor, and proposes that human 5-$HT_6$ receptor is being associated with hematological disorders, pain diseases, respiratory diseases, genito-urological disorders, cardio vascular diseases and cancer.

The present invention also relates to a process for preparing the compound of formula (I), which includes:

Scheme 1—cyclizing a compound of formula (II) given below,

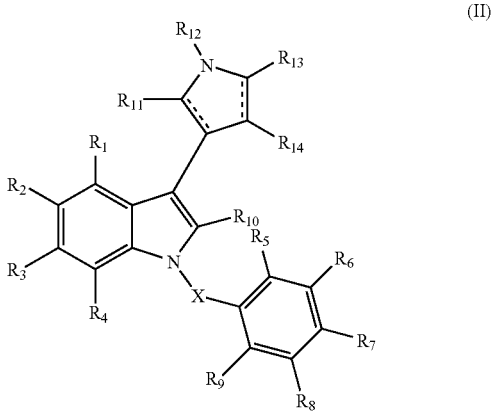

(II)

wherein X can be —CH$_2$—, —CO—, —S—, —S(O), or —S(O)$_2$;

[===] represents either a single or a double bond;

R$_1$, R$_2$, R$_3$, R$_4$, R$_6$, R$_7$, R$_8$ and R$_9$ each independently represent hydrogen, halogen, perhaloalkyl, perhaloalkoxy, hydroxy, (C$_1$-C$_3$)alkyl, (C$_3$-C$_5$)cycloalkyl, (C$_1$-C$_3$)alkoxy, cyclo(C$_3$-C$_5$)alkoxy, aryl, aryloxy, aralkyl, aralkoxy, heterocyclyl, monoalkylamino, dialkylamino or thioalkyl;

R$_{11}$, R$_{12}$, R$_{13}$ and R$_{14}$, each independently represent hydrogen, halogen, oxo, thio, perhaloalkyl, perhaloalkoxy, hydroxy, thiol or (C$_1$-C$_3$)alkyl;

while either of R$_5$ or R$_{10}$ group is a halogen atom such as bromo, chloro or iodo, and the other is hydrogen; using a Pd(0) or Pd (II) derivative as a catalyst, for example tetrakis triphenylphosphine palladium, (Bis-tri-o-tolylphosphine) palladium and optionally base may be needed.

For compounds of formula I and II, suitable groups represented by substitutents like R$_1$, R$_2$, R$_3$, R$_4$, R$_5$, R$_6$, R$_7$, R$_8$, R$_9$, R$_{10}$, R$_{11}$, R$_{12}$, R$_{13}$ and R$_{14}$, whenever applicable, may be selected from: halogen such as fluorine, chlorine, bromine or iodine; perhaloalkyl particularly perhalo(C$_1$-C$_3$) alkyl such as fluoromethyl, difluoromethyl, trifluoromethyl, trifluoroethyl, fluoroethyl, difluoroethyl and the like; substituted or unsubstituted (C$_1$-C$_3$)alkyl group, such as methyl, ethyl, 2-chloroprop-1-yl, iso-propyl and the like; cyclo(C$_3$-C$_5$)alkyl group such as cyclopropyl, cyclobutyl, cyclopentyl, the cycloalkyl group may be substituted; (C$_1$-C$_3$)alkoxy such as methoxy, ethoxy, propyloxy; cyclo(C$_3$-C$_5$) alkoxy group such as cyclopropyloxy, cyclobutyloxy, cyclopentyloxy, the cycloalkoxy group may be substituted; aryl group such as phenyl or naphthyl, the aryl group may be substituted; aryloxy group such as phenyloxy or naphthyloxy, the aryloxy group may be substituted; aralkyl group such as benzyl, phenethyl, C$_6$H$_5$CH$_2$CH$_2$CH$_2$, naphthylmethyl and the like, the aralkyl group may be substituted and the substituted aralkyl is a group such as CH$_3$C$_6$H$_4$CH$_2$, Hal-C$_6$H$_4$CH$_2$, CH$_3$OC$_6$H$_4$CH$_2$, CH$_3$OC$_6$H$_4$CH$_2$CH$_2$ and the like; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; (C$_1$-C$_3$)monoalkylamino group such as CH$_3$NH, C$_2$H$_5$NH, C$_3$H$_7$NH and the like, which may be substituted, (C$_1$-C$_3$) dialkylamino group such as N(CH$_3$)$_2$, CH$_3$(C$_2$H$_5$)N and the like, which may be substituted; thio(C$_1$-C$_3$)alkyl which may be substituted.

The following is a partial list of compounds belonging to general formula (I):

1. (R,S) 10-(1-Methylpyrrolidin-3-yl)-5-thia4b-aza-indeno[2,1-a]indene 5,5-dioxide;
2. (R,S) 10-(1-Ethylpyrrolidin-3-yl)-5-thia4b-aza-indeno[2,1-a]indene 5,5-dioxide;
3. (R,S) 2-Methoxy-10-(1-methylpyrrolidin-3-yl)-5-thia4b-aza-indeno[2,1-a]indene-5,5-dioxide;
4. (R,S) 2-Methoxy-10-(1-ethylpyrrolidin-3-yl)-5-thia-4-b-aza-indeno[2,1-a]indene 5,5-dioxide;
5. (R,S) 1-Methoxy-10-(1-methylpyrrolidin-3-yl)-5-thia4b-aza-indeno[2,1-a]indene 5,5-dioxide;
6. (R,S) 2-Ethoxy-10-(1-methylpyrrolidin-3-yl)-5-thia4b-aza-indeno[2,1-a]indene 5,5-dioxide;
7. (R,S) 2-Ethoxy-10-(1-ethylpyrrolidin-3-yl)-5-thia-4-b-aza-indeno[2,1-a]indene 5,5-dioxide;
8. (R,S) 2-Isopropoxy-10-(1-methylpyrrolidin-3-yl)-5-thia-4b-aza-indeno[2,1-a]indene 5,5-dioxide;
9. (R,S) 1-Isopropoxy-10-(1-ethylpyrrolidin-3-yl)-5-thia-4b-aza-indeno[2,1-a]indene 5,5-dioxide;
10. (R,S) 2-Cyclopentyloxy-10-(1-methylpyrrolidin-3-yl)-5-thia-4b-aza-indeno[2,1-a]indene 5,5-dioxide;
11. (R,S) 3-Methoxy-10-(1-methylpyrrolidin-3-yl)-5-thia-4b-aza-indeno[2,1-a]indene 5,5-dioxide;
12. (R,S) 3-Chloro-10-(1-methylpyrrolidin-3-yl)-5-thia-4b-aza-indeno[2,1-a]indene 5,5-dioxide;
13. (R,S) 10-(1-methylpyrrolidin-3-yl)-5-thia-4b-aza-indeno[2,1-a]indene 5,5-dioxide;
14. (R,S) 2-Methoxy-11-(1-methylpyrrolidin-3-yl)-6H-isoindolo[2,1-a]indole;
15. (S) 10-(1-Methylpyrrolidin-3-yl)-5-thia-4b-aza-indeno[2,1-a]indene 5,5-dioxide;
16. (S) 10-(1-Ethylpyrrolidin-3-yl)-5-thia4b-aza-indeno[2,1-a]indene 5,5-dioxide;
17. (S) 2-Methoxy-10-(1-methylpyrrolidin-3-yl)-5-thia-4b-aza-indeno[2,1-a]indene-5,5-dioxide;
18. (S) 2-Methoxy-10-(1-ethylpyrrolidin-3-yl)-5-thia-4b-aza-indeno[2,1-a]indene 5,5-dioxide;
19. (S) 1-Methoxy-10-(1-methylpyrrolidin-3-yl)-5-thia-4b-aza-indeno[2,1-a]indene 5,5-dioxide;
20. (S) 2-Ethoxy-10-(1-methylpyrrolidin-3-yl)-5-thia4b-aza-indeno[2,1-a]indene 5,5-dioxide;
21. (S) 2-Ethoxy-10-(1-ethylpyrrolidin-3-yl)-5-thia4b-aza-indeno[2,1-a]indene 5,5-dioxide;
22. (S) 2-Isopropoxy-10-(1-methylpyrrolidin-3-yl)-5-thia4b-aza-indeno[2,1-a]indene 5,5-dioxide;
23. (S) 1-Isopropoxy-10-(1-ethylpyrrolidin-3-yl)-5-thia4b-aza-indeno[2,1-a]indene 5,5-dioxide;
24. (S) 2-Cyclopentyloxy-10-(1-methylpyrrolidin-3-yl)-5-thia4b-aza-indeno[2,1-a]indene 5,5-dioxide;
25. (S) 3-Methoxy-10-(1-methylpyrrolidin-3-yl)-5-thia-4b-aza-indeno[2,1-a]indene 5,5-dioxide;
26. (S) 3-Chloro-10-(1-methylpyrrolidin-3-yl)-5-thia4b-aza-indeno[2,1-a]indene 5,5-dioxide;
27. (S) 10-(1-methylpyrrolidin-3-yl)-5-thia-4b-aza-indeno[2,1-a]indene 5,5-dioxide;
28. (S) 2-Methoxy-11-(1-methylpyrrolidin-3-yl)-6H-isoindolo[2,1-a]indole;
29. (R) 10-(1-Methylpyrrolidin-3-yl)-5-thia-4b-aza-indeno[2,1-a]indene 5,5-dioxide;
30. (R) 10-(1-Ethylpyrrolidin-3-yl)-5-thia-4b-aza-indeno[2,1-a]indene 5,5-dioxide;
31. (R) 2-Methoxy-10-(1-methylpyrrolidin-3-yl)-5-thia4b-aza-indeno[2,1-a]indene-5,5-dioxide;
32. (R) 2-Methoxy-10-(1-ethylpyrrolidin-3-yl)-5-thia-4b-aza-indeno[2,1-a]indene 5,5-dioxide;
33. (R) 1-Methoxy-10-(1-methylpyrrolidin-3-yl)-5-thia-4b-aza-indeno[2,1-a]indene 5,5-dioxide;
34. (R) 2-Ethoxy-10-(1-methylpyrrolidin-3-yl)-5-thia-4b-aza-indeno[2,1-a]indene 5,5-dioxide;
35. (R) 2-Ethoxy-10-(1-ethylpyrrolidin-3-yl)-5-thia4b-aza-indeno[2,1-a]indene 5,5-dioxide;
36. (R) 2-Isopropoxy-10-(1-methylpyrrolidin-3-yl)-5-thia-4b-aza-indeno[2,1-a]indene 5,5-dioxide;
37. (R) 1-Isopropoxy-10-(1-ethylpyrrolidin-3-yl)-5-thia4b-aza-indeno[2,1-a]indene 5,5-dioxide;
38. (R) 2-Cyclopentyloxy-10-(1-methylpyrrolidin-3-yl)-5-thia4b-aza-indeno[2,1-a]indene 5,5-dioxide;
39. (R) 3-Methoxy-10-(1-methylpyrrolidin-3-yl)-5-thia-4b-aza-indeno[2,1-a]indene 5,5-dioxide;
40. (R) 3-Chloro-10-(1-methylpyrrolidin-3-yl)-5-thia4b-aza-indeno[2,1-a]indene 5,5-dioxide;
41. (R) 10-(1-methylpyrrolidin-3-yl)-5-thia4b-aza-indeno[2,1-a]indene 5,5-dioxide; and 42. (R) 2-Methoxy-11-(1-methylpyrrolidin-3-yl)-6H-isoindolo[2,1-a]indole;

or a pharmaceutically acceptable salt thereof.

The process of the present invention may also optionally include one or more of the following steps may be further needed to obtain compounds of formula (I):
1. converting a racemic compound of the formula (I) into substantially pure optically active form; or
2. converting one compound of the formula (I) into another; or
3. removing any protecting groups; or
4. forming a pharmaceutically acceptable salt or prodrug thereof.

The present invention further relates to a pharmaceutically acceptable composition comprising at-least one compound of formula (I) in an effective amount along with suitable pharmaceutically acceptable adjuvant, excipient, or diluent.

The present invention also relates to use of one or more compounds defined in above or a composition comprising it, to treat or prevent diseases related to CNS, eating, gastrointestine, blood, pain, respiration, genito-urinary, cardio vascular and cancer, wherein 5-Hydroxytryptamine receptor malfunction is involved.

The present invention also relates to medicaments and their manufacture in various dosage forms, which contain at least one compound of formula (I).

CNS disorders wherein 5-ht receptors are involved and those which could be treated using compounds of this invention include psychosis, paraphrenia, anxiety, depression, mania, schizophrenia, schizophreniform disorders, migraine headache, drug addiction, convulsive disorders, personality disorders, hypertension, autism, post-traumatic stress syndrome, alcoholism, panic attacks, obsessive-compulsive disorders, chronobiological abnormalities and circadian rhythms, cognitive memory disorders e.g. Alzheimer's disease and age-related cognitive decline, ADHD (Attention Deficit Disorder/Hyperactivity Syndrome), amylotrophic lateral sclerosis, withdrawal from drug abuse such as cocaine, ethanol, nicotine and benzodiazepines, panic attacks, and also disorders associated with spinal trauma and/or head injury such as hydrocephalus and also mild cognitive impairment and other neurodegenerative disorders like Alzheimer's disease, Parkinsonism and Huntington's chorea.

GI (Gastrointestinal) disorders wherein 5-ht receptor is involved and such disorders which could be treated using compounds of this invention include IBS (Irritable bowel syndrome) or chemotherapy induced emesis.

Eating behavior is said to be modulated by 5-ht receptor and compounds of this invention can be used to reduce morbidity and mortality associated with the excess weight.

The stereoisomers as a rule are generally obtained as racemates that can be separated into the optically active isomers in a manner known per se. In the case of the compounds of general formula (I) having an asymmetric carbon atom the present invention relates to the R-isomer, S-isomer and R,S-mixtures and in the case of a number of asymmetric carbon atoms, the diastereomeric forms and the invention extends to each of these stereoisomeric forms and to mixtures thereof including racemates. Those compounds of general formula (I) which have an asymmetric carbon and as a rule are obtained as racemates can be separated one from the other by the usual methods, or any given isomer may be obtained by stereospecific or asymmetric synthesis. However, it is also possible to employ an optically active compound from the start, a correspondingly optically active or diastereomeric compound then being obtained as the final compound.

The stereoisomers of compounds of general formula (I) may be prepared by one or more ways presented below:
i) One or more of the reagents may be used in their optically active form.
ii) Optically pure catalyst or chiral ligands along with metal catalyst may be employed in the reduction process. The metal catalysts may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).
iii) The mixture of stereoisomers may be resolved by conventional methods such as forming diastereomeric salts with chiral acids or chiral amines, or chiral amino alcohols, chiral amino acids. The resulting mixture of diastereomers may then be separated by methods such as fractional crystallization, chromatography and the like, which is followed by an additional step of isolating the optically active product by hydrolyzing or neutralizing the derivative (Jacques et. al., "Enantiomers, Racemates and Resolution", Wiley Interscience, 1981). Chiral acids that can be employed may be tartaric acid, mandelic acid, lactic acid, camphorsulfonic acid, amino acids and the like. Chiral bases that can be employed may be cinchona alkaloids, brucine or a compound containing basic amino group such as lysine, arginine and the like.
iv) The mixture of stereoisomers may be resolved by conventional methods such as microbial resolution, resolving the diastereomeric salts formed with chiral acids or chiral bases.

Suitable pharmaceutically acceptable acid addition salts of compounds of the formula (I) can be prepared. The non-toxic acid addition salts include those having pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benezenesulfonate, p-toluenesulfonate, palmoate and oxalate. Pharmaceutically acceptable salts forming part of this invention are intended to define but not limited to the above list.

In addition, pharmaceutically acceptable salts of the compound of general formula (I) can be obtained by converting derivatives which have tertiary amino groups into the corresponding quarternary ammonium salts in the methods known in the literature by using quarternizing agents. Possible quarternizing agents are, for example, alkyl halides such as methyl iodide, ethyl bromide and n-propyl chloride, including arylalkyl halides such as benzyl chloride or 2-phenylethyl bromide.

The pharmaceutically acceptable salts forming a part of this invention may be prepared by treating the compound of formula (I) with 1-6 equivalents of a acid mentioned as above in solvents such as water, alcohols, ethers, ethyl acetate, dioxane, DMF or a lower alkyl ketone such as acetone, or the mixtures thereof.

Further the exceptional salts may be formed as intermediates during purification, preparation of other salts, or identification and characterization of compounds of formula (I) or intermediates involved in preparing compounds of formula (I).

The pharmaceutically acceptable salts of compounds of formula (I) may exist as solvates, such as with water, methanol, ethanol, dimethylformamide, ethyl acetate, and the like. The source of such solvate can be from the solvent of crystallization, inherent in the solvent preparation or crystallization, or adventitious to such solvent.

There may be need to prepare radio-labeled compounds related to general structure (I). Suitable isotopes which can be prepared by incorporating isotopes of hydrogen, carbon, nitrogen, oxygen, phosphorus, fluorine, chlorine, iodine, bromine and mTecnitium, exemplified by $^{2}H$, $^{3}H$, $^{11}C$, $^{13}C$, $^{14}C$, $^{13}N$, $^{15}N$, $^{15}O$, $^{18}F$, $^{99m}Tc$, $^{31}P$, S, $^{123}I$ and $^{125}I$. These compounds containing the aforementioned isotopes and/or other isotopes of other atoms are within the scope of this invention. Isotopically labeled compounds of the present invention are popular in drug and/or substrate tissue distribution and target occupancy assays. For example, isotopically labeled compounds are particularly useful in SPECT (single photon emission computed tomography) and in PET (positron emission tomography).

Another aspect of the present invention comprises of a pharmaceutical composition, containing at least one of the compounds of general formula (I) as defined earlier, either in pure or impure forms forming an active ingredient, together with pharmaceutically employed carriers, auxiliaries and the like.

An effective amount of a compound of general formula (I), or their derivatives as defined above can be used to produce a medicament, along with conventional pharmaceutical auxiliaries, carriers and additives. "Therapeutically effective amount" is defined as 'an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein'.

Such therapy includes multiple choices: for example, administering two compatible compounds simultaneously in a single dose form or administering each compound individually in a separate dosage; or if required at same time interval or separately in order to maximize the beneficial effect or minimize the potential side-effects of the drugs according to the known principles of pharmacology.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace all the meanings such as inhibitory or inhibit, preventative, prophylactic and palliative.

The pharmaceutical compositions of the present invention may be formulated in a conventional manner using one or more pharmaceutically acceptable carriers. Thus, the active compounds of the invention may be formulated for oral, buccal, intranasal, parental (e.g., intravenous, intramuscular or subcutaneous) or rectal administration or a form suitable for administration by inhalation or insufflation.

The pharmaceutical compositions as well as the formulated medicaments prepared according to the present invention may in addition to at least one compound of formula (I), optionally in form of one of its stereoisomers, preferably enantiomers or diastereomers, its racemate or in form of a mixture of at least two of its stereoisomers, preferably enantiomers or diastereomers, in any mixing ratio, or a corresponding physiologically acceptable salt or a corresponding solvate, comprise further conventional auxiliary substances known to those skilled in the art, such as carriers, fillers, solvents, diluents, colouring agents, coating agents, matrix agents and/or binders. As is also known to those skilled in the art, the choice of the auxiliary substances and the amounts thereof to be used are dependent on the intended route of administration, e.g. oral, rectal, intravenous, intraperitoneal, intramuscular, intranasal, buccal or topical route.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

Medicaments suitable for parenteral, topical or inhalatory administration may preferably be selected from the group consisting of solutions, suspensions, readily reconstitutable dry preparations and also sprays.

Suitable medicaments, e.g. medicaments for oral or percutaneous use may release the sulphonamide compounds of general formula (I) in a delayed manner, whereby the preparation of these delayed release medicaments is generally known to those skilled in the art.

Medicaments suitable for oral administration are for example, tablets, sugar-coated pills, capsules or multiparticulates, such as granules or pellets, optionally compressed into tablets, filled into capsules or suspended in a suitable liquid, solutions or suspensions. Such the pharmaceutical compositions may have excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer, or from a capsule using a inhaler or insufflator. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule it preferably should be in the form of powder. Capsules and cartridges (made, for example, from gelatin) for use in an inhaler or insufflator may be formulated containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

Suitable delayed-release forms as well as materials and methods for their preparation are known to those skilled in the art, e.g. from the tables of contents from "Modified-Release Drug Delivery Technology", Rathbone, M. J. Hadgraft, J. and Roberts, M. S. (Eds.), Marcel Dekker, Inc., New York (2002); "Handbook of Pharmaceutical Controlled Release Technology", Wise, D. L. (Ed.), Marcel Dekker, Inc. New York, (2000); "Controlled Drug Delivery", Vol. 1, Basic Concepts, Bruck, S. D. (Ed.), CRC Press Inc., Boca Raton (1983) and from Takada, K. and Yoshikawa, H., "Oral Drug delivery", Encyclopedia of Controlled Drug Delivery, Mathiowitz, E. (Ed.), John Wiley & Sons, Inc., New York (1999), Vol. 2, 728-742; Fix, J., "Oral drug delivery, small intestine and colon", Encyclopedia of Controlled Drug Delivery, Mathiowitz, E. (Ed.), John Wiley & Sons, Inc., New York (1999), Vol. 2, 698 The respective descriptions are incorporated by reference and are part of the disclosure.

The medicament of the present invention may also have at least one enteric coating, which dissolves as a function of pH. Because of this coating, the medicament can pass through the stomach undissolved and the compounds of general formula I are only released in the intestinal tract. The enteric coating preferably dissolves at a pH of between 5 and 7. Suitable materials and methods for the preparation of enteric coatings are also known to those skilled in the art. Typically the pharmaceutical compositions and medicaments comprise 1 to 60% by weight of one or more sulphonamide derivatives of general formula (I) and 40 to 99% by weight of one or more excipients.

The preparation of corresponding pharmaceutical compositions as well as of the formulated medicaments may be carried out by conventional methods known to those skilled in the art, e.g. from the tables of contents from "Pharmaceutics: the Science of Dosage Forms", Second Edition, Aulton, M. E. (Ed.) Churchill Livingstone, Edinburgh (2002); "Encyclopedia of Pharmaceutical Technology", Second Edition, Swarbrick, J. and Boylan J. C. (Eds.), Marcel Dekker, Inc. New York (2002); "Modern Pharmaceutics", Fourth Edition, Banker G. S. and Rhodes C. T. (Eds.) Marcel Dekker, Inc. New York 2002; and "The Theory and Practice of Industrial Pharmacy", Lachman L., Lieberman H. and Kanig J. (Eds.), Lea & Febiger, Philadelphia (1986). The respective literature descriptions are incorporated by reference and are part of the disclosure.

For illustrative purposes, the reaction schemes depicted herein provide potential routes for synthesizing the compounds of the present invention as well as key intermediates. For a more detailed description of the individual reaction steps, see the Examples section.

Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

The following description illustrates the method of preparation of variously substituted compounds of general formula (I), according to the methods described herein. Further examples of the receptor binding and biological evaluation are provided by the way of illustration only and therefore should not be construed to limit the scope of the invention.

EXAMPLES

Commercial reagents were utilized without further purification. Room temperature refers to 25-30° C. Melting points are uncorrected. IR spectra were taken using KBr and in solid state. Unless otherwise stated, all mass spectra were carried out using ESI conditions. 1H NMR spectra were recorded at 400 MHz on a Bruker instrument. Deuterated chloroform (99.8% D) was used as solvent. TMS was used as internal reference standard. Chemical shift values are expressed in parts per million (δ)-values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. NMR, mass were corrected for background peaks. Specific rotations were measured at room temperature using the sodium D (589 nm). Chromatography refers to column chromatography performed using 60-120 mesh silica gel and executed under nitrogen pressure (flash chromatography) conditions.

Example-1

(R,S) 10-(1-Methylpyrrolidin-3-yl)-5-thia-4b-aza-indeno[2,1-a]indene 5,5-dioxide

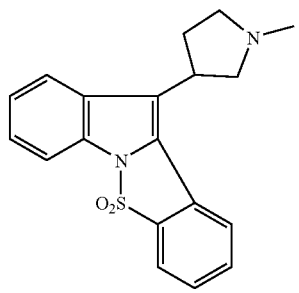

A stirred solution of 1-Benzenesulfonyl-3-(1-methylpyrrolidin-3-yl)-1H-indole (0.286 moles) was taken in a 100 mL 3 necked round bottomed flask, along with N,N-dimethyl acetamide (40 mL), potassium acetate (0.286 moles, 0.281 g) and dichloro bis(tri-o-tolylphosphine)palladium (0.0143 moles, 0.0126 g). The reaction mixture was maintained under nitrogen atmosphere and was heated to 160° C. with stirring for 16 hrs. After the completion of reaction, excess of dimethyl acetamide was distilled off under reduced pressure and the residue was purified by silica gel column chromatography using 20% methanol in ethyl acetate as an eluent. The final desired compound of general formula (I) could be further purified by preparation of their acid addition salts. IR spectra (cm−1): 2940.65, 1325.79, 1181.79, 583.29; Mass (m/z): 339 (M+H)$^+$; $^1$H-NMR (ppm): 2.20-2.25 (1H, m), 2.33-2.37 (1H, m), 2.50 (3H, s), 2.83-2.97 (4H, m), 4.02-4.07 (1H, m), 7.250-7.253 (1H, m), 7.38-7.48 (2H, m), 7.670-7.672 (1H, m), 7.70-7.72 (1H, d), 7.83-7.89 (2H, d), 8.05-8.07 (1H, d), Melting range (° C.): 167.8-173.1

Example-2

(R,S) 10-(1-Ethylpyrrolidin-3-yl)-5-thia4b-aza-indeno[2,1-a]indene 5,5-dioxide

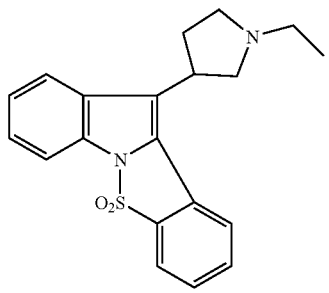

Using essentially the general procedure described in example 1 and some non-critical variations, the above derivative was prepared. IR spectra (cm−1): 2924.70, 1334.60, 1180.99, 582.08; Mass (m/z): 353 (M+H)$^+$; $^1$H-NMR (ppm): 1.28 (3H, s), 1.32-1.36 (1H, m), 2.25 (1H, m), 2.36-2.39 (1H, m), 2.75 (1H, m), 2.96-3.01 (1H, m), 3.45 (3H, m), 4.05-4.09 (1H, m), 7.23 (1H, m), 7.36-7.40 (1H, m0, 7.46-7.50 (1H, t), 7.65-7.73 (2H, m), 7.83-7.86 (2H, t), 8.12-8.13 (1H, d); Melting range (° C.): 97.7-106.8

Example-3

(R,S) 2-Methoxy-10-(1-methylpyrrolidin-3-yl)-5-thia-4b-aza-indeno[2,1-a]indene 5,5-dioxide

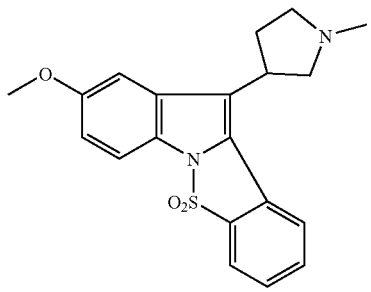

Using essentially the general procedure described in example 1 and some non-critical variations, the above derivative was prepared. IR spectra (cm−1): 2796.60, 1325.04, 1165.97, 580.47; Mass (m/z): 369 (M+H)$^+$; $^1$H-NMR (ppm): 2.16-2.21 (1H, m), 2.32-2.35 (1H, m), 2.48 (3H, s), 2.75-2.77 (1H, q), 2.82-2.87 (1H, t), 2.93-2.97 (2H, m), 3.86 (3H, s), 3.97-4.01 (1H, m), 6.98-7.01 (1H, dd), 7.44-7.48 (2H, m), 7.58-7.61 (1H, d), 7.63-7.67 (1H, m), 7.81-7.83 (1H, d), 8.01-8.03 (1H, d); Melting range (° C.): 132.3-143.5.

Example-4

(R,S) 2-Methoxy-10-(1-ethylpyrrolidin-3-yl)-5-thia4b-aza-indeno[2,1-a]indene 5,5-dioxide

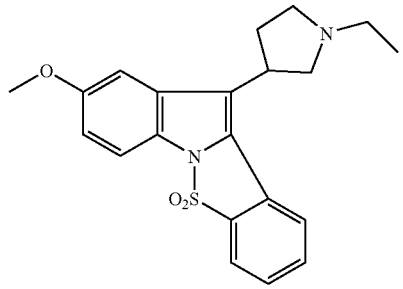

Using essentially the general procedure described in example 1 and some non-critical variations, the above derivative was prepared. IR spectra (cm−1): 2967.25, 1332.38, 1178.78, 580.50; Mass (m/z): 383 (M+H)$^+$; $^1$H-NMR (ppm): 1.12-1.16 (3H, t), 1.97 (1H, m), 2.21 (1H, m), 2.35-2.37 (1H, m), 2.71-2.72 (3H, m), 3.00-3.02 (2H, q), 3.87 (3H, s), 4.03-4.05 (1H, m), 6.69-7.01 (1H, dd), 7.44-7.48 (2H, m), 7.59-7.61 (1H, d), 7.63-7.66 (1H, m), 7.81-7.83 (1H, d), 8.06-8.08 (1H, d); Melting range (° C.): 98.8 108.8 (Not clear).

Example-5

(R,S) 1-Methoxy-10-(1-methylpyrrolidin-3-yl)-5-thia4b-aza-indeno[2,1-a]indene 5,5-dioxide

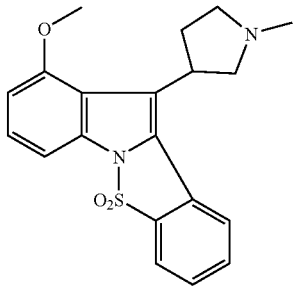

Using essentially the general procedure described in example 1 and some non-critical variations, the above derivative was prepared. IR spectra (cm−1): 2938.51, 1330.88, 1182.16, 582.69; Mass (m/z): 369 (M+H)$^+$; $^1$H-NMR (ppm): 2.20-2.23 (1H, m), 2.33-2.35 (1H, m), 2.51 (3H, s), 2.78-2.81 (1H, m), 2.87-2.92 (1H, t), 3.01-3.05 (2H, m), 3.96 (3H, s), 4.32-4.36 (1H, m), 6.67-6.69 (1H, dd), 7.28-7.34 (2H, m), 7.43-7.47 (1H, t), 7.63-7.67 (1H, t), 7.80-7.82 (1H, d), 8.25-8.27 (1H, d); Melting range (° C.): 117.1-124.1.

Example-6

(R,S) 2-Ethoxy-10-(1-methylpyrrolidin-3-yl)-5-thia-4b-aza-indeno[2,1-a]indene 5,5-dioxide

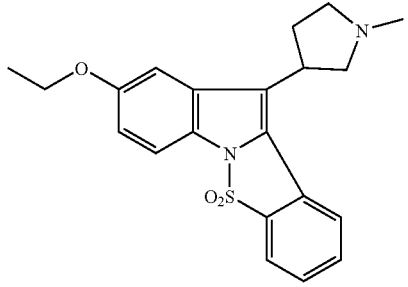

Using essentially the general procedure described in example 1 and some non-critical variations, the above derivative was prepared. IR spectra (cm−1): 2922.71, 1329.37, 1175.85, 559.38; Mass (m/z): 383 (M+H)$^+$; $^1$H-NMR (ppm): 1.42-1.47 (3H t), 2.18-2.22 (1H, m), 2.32-2.43 (1H, m), 2.49 (3H, s), 2.77-2.79 (1H, m), 2.86-2.88 (1H, m), 2.92-2.95 (2H, m), 3.89-3.99 (1H, m), 4.06-4.11 (2H, q), 6.98-7.01 (1H, dd), 7.44-7.48 (2H, m), 7.57-7.60 (1H, d), 7.62-7.66 (1H, t), 7.80-7.83 (1H, m), 8.01-8.03 (1H, m); Melting range (° C.): 115.9-118.9.

Example-7

(R,S) 2-Ethoxy-10-(1-ethylpyrrolidin-3-yl)-5-thia4b-aza-indeno[2,1-a]indene 5,5-dioxide

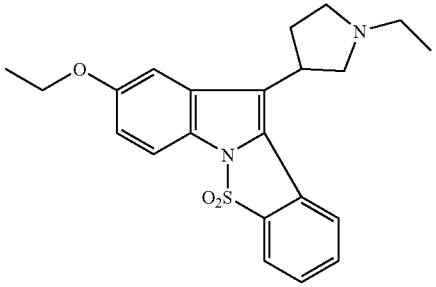

Using essentially the general procedure described in example 1 and some non-critical variations, the above derivative was prepared. IR spectra (cm−1): 2966.41, 1328.87, 1179.74, 559.05; Mass (m/z): 397 (M+H)$^+$; $^1$H-NMR (ppm): 1.17-1.21 (3H, t), 1.44-1.47 (3H, t), 2.18-2.19 (1H, m), 2.32-2.38 (1H, m), 2.59-2.68 (2H, m), 2.74-2.80 (1H, m), 2.88-2.90 (1H, t), 2.95-2.99 (2H, m), 4.06-4.11 (3H, m), 6.982-6.988 (1H, dd), 7.44-7.48 (2H, m), 7.57-7.60 (1H, d), 7.62-7.64 (1H, m), 7.80-7.82 (1H, m), 8.05-8.07 (1H, m); Melting range (° C.): 110.0-115.1.

Example-8

(R,S) 2-Isopropoxy-10-(1-methylpyrrolidin-3-yl)-5-thia4b-aza-indeno[2,1-a]indene 5,5-dioxide

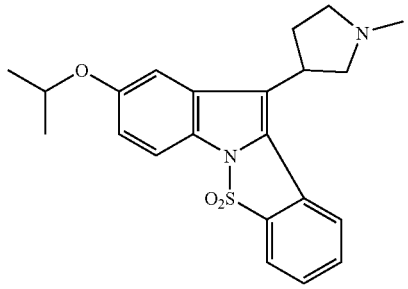

Using essentially the general procedure described in example 1 and some non-critical variations, the above derivative was prepared. IR spectra (cm−1): 2972.78, 1325.35, 1180.78, 586.00; Mass (m/z): 397 (M+H)$^+$; $^1$H-NMR (ppm): 1.36-1.38 (6H, d), 2.17-0.20 (1H, m), 2.33 (1H, m), 2.48 (3H, s), 2.74-2.76 (1H, m), 2.81-2.83 (1H, t), 2.90-2.94 (2H, m), 3.95-3.97 (1H, m), 4.53-4.56 (1H, m), 6.97-6.99 (1H, dd), 7.46-7.49 (2H, m), 7.57-7.59 (1H, d), 7.62-7.64 (1H, m), 7.81-7.82 (1H, d), 8.00-8.01 (1H, d); Melting range (° C.): 141.8-145.7.

Example-9

(R,S) 1-Isopropoxy-10-(1-ethylpyrrolidin-3-yl)-5-thia4b-aza-indeno[2,1-a]indene 5,5-dioxide

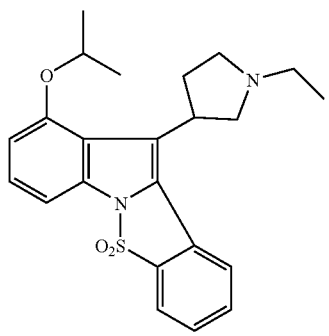

Using essentially the general procedure described in example 1 and some non-critical variations, the above derivative was prepared. IR spectra (cm−1): 2970.99, 1335.29, 1182.51, 580.92; Mass (m/z): 411 (M+H)$^+$; $^1$H-NMR (ppm): 1.25 (3H, m) 1.45-1.47 (6H, d), 2.27-2.29 (2H, m), 2.72-2.74 (1H, m), 2.84-2.86 (1H, t), 2.92-2.95 (2H, m), 3.04-3.06 (1H, m), 3.15-3.17 (1H, m), 4.45-4.48 (1H, m), 4.76-4.82 (1H, m), 6.67-6.69 (1H, d), 7.24-7.30 (2H, m), 7.42-7.46 (1H, t), 7.63-7.67 (1H, t), 7.79-7.81 (1H, d), 8.56-8.58 (1H, d); Melting range (° C.): 133.4-139.7.

Example-10

(R,S) 2-Cyclopentyloxy-10-(1-methylpyrrolidin-3-yl)-5-thia-4b-aza-indeno[2,1-a]indene 5,5-dioxide

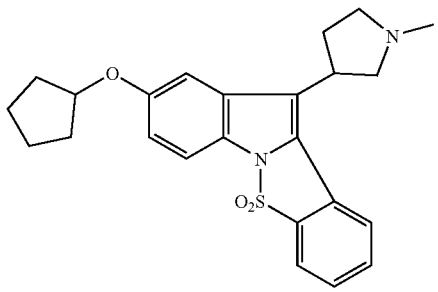

Using essentially the general procedure described in example 1 and some non-critical variations, the above derivative was prepared. IR spectra (cm−1): 2955.86, 1324.77, 1180.75, 586.63; Mass (m/z): 423 (M+H)+; H-NMR (ppm): 1.63-1.66 (2H, m), 1.83-1.94 (6H, m), 2.18-2.26 (1H, m), 2.32-2.41 (1H, m), 2.48 (3H, s), 2.68-2.74 (1H, m), 2.78-2.82 (1H, t), 2.91-2.95 (2H, m), 3.96-4.04 (1H, m0, 4.76-4.78 (1H, m), 6.94-6.97 (1H, dd), 7.43-7.47 (2H, m), 7.56-7.58 (1H, d), 7.62-7.66 (1H, m), 7.80-7.82 (d, 1H), 7.98-8.00 (1H, d); Melting range (° C.): 176.4-180.2.

Example-11

(R,S) 3-Methoxy-10-(1-methylpyrrolidin-3-yl)-5-thia4b-aza-indeno[2,1-a]indene 5,5-dioxide

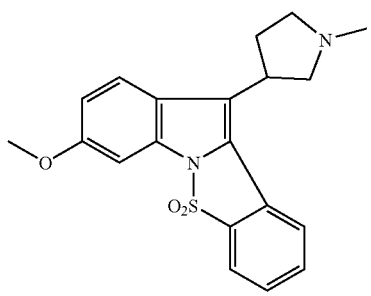

Using essentially the general procedure described in example 1 and some non-critical variations, the above derivative was prepared. IR spectra (cm−1): 2924.59, 1333.23, 1183.39, 590.00; Mass (m/z): 369 (M+H)+.

Example-12

(R,S) 3-Chloro-10-(1-methylpyrrolidin-3-yl)-5-thia4b-aza-indeno[2,1-a]indene 5,5-dioxide

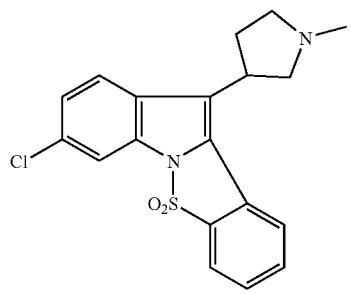

Using essentially the general procedure described in example 1 and some non-critical variations, the above derivative was prepared. IR spectra (cm−1): 2925.28, 1337.48, 1181.26, 585.32; Mass (m/z): 373 (M+H)+, 375 (M+3)+.

Example-13

(R,S) 10-(1-methylpyrrolidin-3-yl)-5-thia4b-aza-indeno[2,1-a]indene 5,5-dioxide

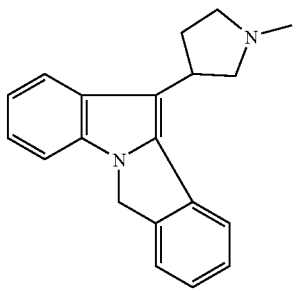

Using essentially the general procedure described in example 1 and some non-critical variations, the above derivative was prepared. IR spectra (cm−1): 2768.42, 1469.12, 1445.60, 742.41; Mass (m/z): 289 (M+H)+; $^1$H-NMR (ppm): 2.21-2.41 (2H, m), 2.52 (3H, s), 2.85-2.89 (2H, m), 3.02-3.05 (2H, m), 4.09-4.18 (1H, m), 5.04 (2H, s), 7.09-7.11 (1H, m), 7.18-7.20 (1H, m), 7.28-7.34 (2H, m), 7.38-7.46 (2H, m), 7.79-7.81 (1H, d), 7.90-7.92 (1H, d).

Example-14

(R,S) 2-Methoxy-11-(1-methylpyrrolidin-3-yl)-6H-isoindolo[2,1-a]indole

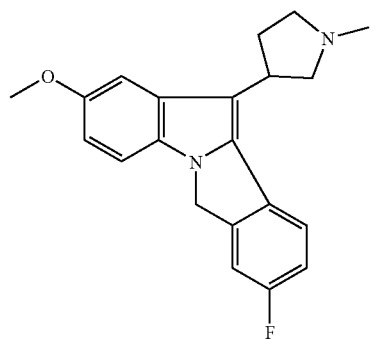

Using essentially the general procedure described in example 1 and some non-critical variations, the above derivative was prepared. IR spectra (cm−1): 2935.40, 1472.68, 1435.62, 752.08; Mass (m/z): 337 (M+H)+; $^1$H-NMR (ppm): 2.38-2.42 (2H, m), 2.59 (3H, s), 3.01-3.10 (4H, m), 3.89 (3H, s), 4.07-4.09 (1H, m), 4.97 (2H, s), 6.87-6.90 (1H, m), 6.96-6.97 (1H, m), 7.21-7.23 (1H, d), 7.28-2.29 (1H, d), 7.35-7.38 (1H, m), 7.63-7.66 (1H, dd).

Example-15

Food Intake Measurement

Male Wistar rats (100-270 g) obtained from (National Institute of Nutrition, Hyderabad, India) are used. The animals are acclimatized to the animal facility for at least 7 days before they are subjected to any treatment. During this period the animals are housed (in groups of three) in translucid cages and provided with food and water ad libitum. At least 24 hours before the treatment starts, the animals are adapted to single-housing conditions.

The chronic effect of the compounds of general formula (I) on food intake in well-fed rats is then determined as follows. The rats were housed in their single homecages for 28 days. After this period, the rats are orally dosed with a composition comprising a compound of formula (1) or a corresponding composition (vehicle) without said compound, once-a-day. The rat is provided with ad libitum food and water. On 0, $7^{th}$, $14^{th}$, $21^{st}$ and $28^{th}$ day the rat is left with preweighed food. Food intake and weight gain is measured.

Example-16

Tablet Comprising a Compound of Formula (I)

| Ingredient | Amount |
| --- | --- |
| Compound according to example 1 | 5 mg |
| Lactose | 60 mg |
| Crystalline cellulose | 25 mg |
| K 90 Povidone | 5 mg |
| Pregelatinised starch | 3 mg |
| Colloidal silicon dioxide | 1 mg |
| Magnesium stearate | 1 mg |
| Total weight per tablet | 100 mg |

The ingredients are combined and granulated using a suitable solvent such as ethanol. The formulation is then dried and formed into tablets (containing about 20 mg of active compound) with an appropriate tablet machine.

Example-17

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example-18

Liquid Oral Formulation

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 g |
| Colorings | 0.5 g |
| Distilled water | q.s. to 100 ml |

The ingredients are mixed to form a suspension for oral administration.

Example-19

Parenteral Formulation

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example-20

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example-21

Topical Formulation

| Ingredients | grams |
| --- | --- |
| Active compound | 0.2-2 g |
| Span 60 | 2 g |
| Tween 60 | 2 g |
| Mineral oil | 5 g |
| Petrolatum | 10 g |
| Methyl paraben | 0.15 g |
| Propyl paraben | 0.05 g |
| BHA (butylated hydroxy anisole) | 0.01 g |
| Water | 100 ml |

All of the ingredients, except water, are combined and heated to about 60° C. with stirring. A sufficient quantity of water at about 60° C. is then added with vigorous stirring to emulsify the ingredients, and water then added q.s. about 100 g.

Example-22

Binding Assay for Human $5HT_6$ Receptor

Materials and Methods:
Receptor source: Human recombinant expressed in HEK293 cells
Radioligand: [$^3$H]LSD (60-80 Ci/mmol)
Final ligand concentration—[1.5 nM]
Non-specific determinant: Methiothepin mesylate—[0.1 µM]
Reference compound: Methiothepin mesylate
Positive control: Methiothepin mesylate Incubation Conditions:
Reactions are carried out in 50 mM TRIS-HCl (pH 7.4) containing 10 mM $MgCl_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound(s) with the cloned serotonin—$5HT_6$ binding site.

LITERATURE REFERENCE

Monsma F. J. Jr., et al., Molecular Cloning and Expression of Novel Serotonin Receptor with High Affinity for Tricyclic Psychotropic Drugs. Mol. Pharmacol. (43): 320-327 (1993).

| Structure | Ki nM | IC50 µM |
|---|---|---|
| 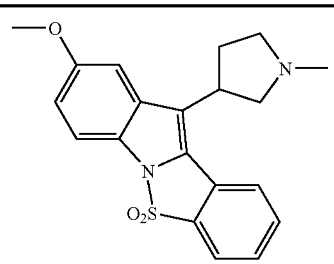 | 88.10 | 0.205 |
| 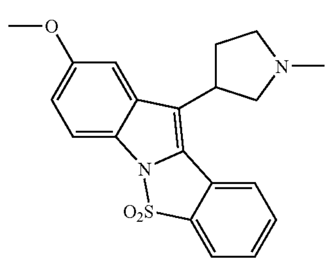 | 172.00 | 0.383 |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:
1. A compound of formula I:

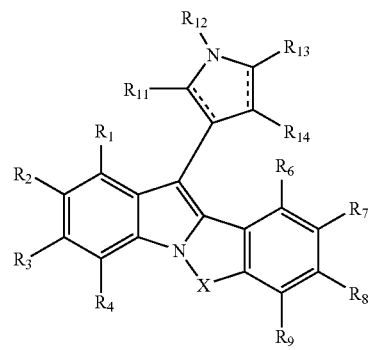

(I)

wherein:
X is —$CH_2$—, —CO—, —S—, —S(O)—, or —$S(O)_2$—;
the bonds represented by ═══ are independently single or double bonds;
each of $R_1$, $R_2$, $R_3$, $R_4$, $R_6$, $R_7$, $R_8$ and $R_9$ are independently hydrogen, halogen, perhaloalkyl, perhaloalkoxy, hydroxy, ($C_1$-$C_3$)alkyl, ($C_3$-$C_5$)cycloalkyl, ($C_1$-$C_3$) alkoxy, cyclo($C_3$-$C_5$)alkoxy, aryl, aryloxy, aralkyl, aralkoxy, heterocyclyl, monoalkylamino, dialkylamino, or thioalkyl; and
each of $R_{11}$, $R_{12}$, $R_{13}$ and $R_{14}$, are independently hydrogen, halogen, oxo, thio, perhaloalkyl, perhaloalkoxy, hydroxy, thiol, or ($C_1$-$C_3$)alkyl;
or a pharmaceutically acceptable salt or a stereoisomer thereof.

2. The compound of claim 1, wherein the compound of formula I is:
(R,S) 10-(1-Methylpyrrolidin-3-yl)-5-thia-4b-aza-indeno[2,1-a]indene 5,5-dioxide;
(R,S) 10-(1-Ethylpyrrolidin-3-yl)-5-thia-4b-aza-indeno[2,1-a]indene 5,5-dioxide;
(R,S) 2-Methoxy-10-(1-methylpyrrolidin-3-yl)-5-thia-4b-aza-indeno[2,1-a]indene-5,5-dioxide;
(R,S) 2-Methoxy-10-(1-ethylpyrrolidin-3-yl)-5-thia-4b-aza-indeno[2,1-a]indene 5,5-dioxide;
(R,S) 1-Methoxy-10-(1-methylpyrrolidin-3-yl)-5-thia-4b-aza-indeno[2,1-a]indene 5,5-dioxide;
(R,S) 2-Ethoxy-10-(1-methylpyrrolidin-3-yl)-5-thia-4b-aza-indeno[2,1-a]indene 5,5-dioxide;
(R,S) 2-Ethoxy-10-(1-ethylpyrrolidin-3-yl)-5-thia-4b-aza-indeno[2,1-a]indene 5,5-dioxide;
(R,S) 2-Isopropoxy-10-(1-methylpyrrolidin-3-yl)-5-thia-4b-aza-indeno[2,1-a]indene 5,5-dioxide;
(R,S) 1-Isopropoxy-10-(1-ethylpyrrolidin-3-yl)-5-thia-4b-aza-indeno[2,1-a]indene 5,5-dioxide;
(R,S) 2-Cyclopentyloxy-10-(1-methylpyrrolidin-3-yl)-5-thia-4b-aza-indeno[2,1-a]indene 5,5-dioxide;
(R,S) 3-Methoxy-10-(1-methylpyrrolidin-3-yl)-5-thia-4b-aza-indeno[2,1-a]indene 5,5-dioxide;
(R,S) 3-Chloro-10-(1-methylpyrrolidin-3-yl)-5-thia-4b-aza-indeno[2,1-a]indene 5,5-dioxide;
(R,S) 10-(1-methylpyrrolidin-3-yl)-5-thia-4b-aza-indeno[2,1-a]indene 5,5-dioxide;
(R,S) 2-Methoxy-1-(1-methylpyrrolidin-3-yl)-6H-isoindolo[2,1-a]indole;
(S) 10-(1-Methylpyrrolidin-3-yl)-5-thia-4b-aza-indeno[2,1-a]indene 5,5-dioxide;

(S) 10-(1-Ethylpyrrolidin-3-yl)-5-thia-4b-aza-indeno[2,1-a]indene 5,5-dioxide;

(S) 2-Methoxy-10-(1-methylpyrrolidin-3-yl)-5-thia-4b-aza-indeno[2,1-a]indene-5,5-dioxide;

(S) 2-Methoxy-10-(1-ethylpyrrolidin-3-yl)-5-thia-4b-aza-indeno[2,1-a]indene 5,5-dioxide;

(S) 1-Methoxy-10-(1-methylpyrrolidin-3-yl)-5-thia-4b-aza-indeno[2,1-a]indene 5,5-dioxide;

(S) 2-Ethoxy-10-(1-methylpyrrolidin-3-yl)-5-thia-4b-aza-indeno[2,1-a]indene 5,5-dioxide;

(S) 2-Isopropoxy-10-(1-ethylpyrrolidin-3-yl)-5-thia-4b-aza-indeno[2,1-a]indene 5,5-dioxide;

(S) 2-Isopropoxy-10-(1-methylpyrrolidin-3-yl)-5-thia-4b-aza-indeno[2,1-a]indene 5,5-dioxide;

(S) 1-Isopropoxy-10-(1-ethylpyrrolidin-3-yl)-5-thia-4b-aza-indeno[2,1-a]indene 5,5-dioxide;

(S) 2-Cyclopentyloxy-10-(1-methylpyrrolidin-3-yl)-5-thia-4b-aza-indeno[2,1-a]indene 5,5-dioxide;

(S) 3-Methoxy-10-(1-methylpyrrolidin-3-yl)-5-thia-4b-aza-indeno[2,1-a]indene 5,5-dioxide;

(S) 3-Chloro-10-(1-methylpyrrolidin-3-yl)-5-thia-4b-aza-indeno[2,1-a]indene 5,5-dioxide;

(S) 10-(1-methylpyrrolidin-3-yl)-5-thia-4b-aza-indeno[2,1-a]indene 5,5-dioxide;

(S) 2-Methoxy-11-(1-methylpyrrolidin-3-yl)-6H-isoindolo[2,1-a]indole;

(R) 10-(1-Methylpyrrolidin-3-yl)-5-thia-4b-aza-indeno[2,1-a]indene 5,5-dioxide;

(R) 10-(1-Ethylpyrrolidin-3-yl)-5-thia-4b-aza-indeno[2,1-a]indene 5,5-dioxide;

(R) 2-Methoxy-10-(1-methylpyrrolidin-3-yl)-5-thia-4b-aza-indeno[2,1-a]indene-5,5-dioxide;

(R) 2-Methoxy-10-(1-ethylpyrrolidin-3-yl)-5-thia-4b-aza-indeno[2,1-a]indene 5,5-dioxide;

(R) 1-Methoxy-10-(1-methylpyrrolidin-3-yl)-5-thia-4b-aza-indeno[2,1-a]indene 5,5-dioxide;

(R) 2-Ethoxy-10-(1-methylpyrrolidin-3-yl)-5-thia-4b-aza-indeno[2,1-a]indene 5,5-dioxide;

(R) 2-Ethoxy-10-(1-ethylpyrrolidin-3-yl)-5-thia-4b-aza-indeno[2,1-a]indene 5,5-dioxide;

(R) 2-Isopropoxy-10-(1-methylpyrrolidin-3-yl)-5-thia-4b-aza-indeno[2,1-a]indene 5,5-dioxide;

(R) 1-Isopropoxy-10-(1-ethylpyrrolidin-3-yl)-5-thia-4b-aza-indeno[2,1-a]indene 5,5-dioxide;

(R) 2-Cyclopentyloxy-10-(1-methylpyrrolidin-3-yl)-5-thia-4b-aza-indeno[2,1-a]indene 5,5-dioxide;

(R) 3-Methoxy-10-(1-methylpyrrolidin-3-yl)-5-thia-4b-aza-indeno[2,1-a]indene 5,5-dioxide;

(R) 3-Chloro-10-(1-methylpyrrolidin-3-yl)-5-thia-4b-aza-indeno[2,1-a]indene 5,5-dioxide;

(R) 10-(1-methylpyrrolidin-3-yl)-5-thia-4b-aza-indeno[2,1-a]indene 5,5-dioxide;

(R) 2-Methoxy-11-(1-methylpyrrolidin-3-yl)-6H-isoindolo[2,1-a]indole;

or a pharmaceutically acceptable salt thereof.

3. A method for preparing a compound of formula I:

(I)

wherein:
X is —CH$_2$—, —CO—, —S—, —S(O)—, or —S(O)$_2$—;
the bonds represented by ═══ are independently single or double bonds;
each of R$_1$, R$_2$, R$_3$, R$_4$, R$_6$, R$_7$, R$_8$ and R$_9$ are independently hydrogen, halogen, perhaloalkyl, perhaloalkoxy, hydroxy, (C$_1$-C$_3$)alkyl, (C$_3$-C$_5$)cycloalkyl, (C$_1$-C$_3$) alkoxy, cyclo(C$_3$-C$_5$)alkoxy, aryl, aryloxy, aralkyl, aralkoxy, heterocyclyl, monoalkylamino, dialkylamino, or thioalkyl; and
each of R$_{11}$, R$_{12}$, R$_{13}$ and R$_{14}$, are independently hydrogen, halogen, oxo, thio, perhaloalkyl, perhaloalkoxy, hydroxy, thiol, or (C$_1$-C$_3$)alkyl;
or a pharmaceutically acceptable salt or a stereoisomers thereof, comprising:
contacting a compound of formula (II) with a Pd(0) or Pd(II) catalyst to effect a cyclization, wherein the compound of formula II is:

(II)

wherein:
X is —CH$_2$—, —CO—, —S—, —S(O)—, or —S(O)$_2$—;
the bonds represented by ═══ are independently single or double bonds;
each of R$_1$, R$_2$, R$_3$, R$_4$, R$_6$, R$_7$, R$_8$ and R$_9$ are independently hydrogen, halogen, perhaloalkyl, perhaloalkoxy, hydroxy, (C$_1$-C$_3$)alkyl, (C$_3$-C$_5$)cycloalkyl, (C$_1$-C$_3$) alkoxy, cyclo(C$_3$-C$_5$)alkoxy, aryl, aryloxy, aralkyl, aralkoxy, heterocyclyl, monoalkylamino, dialkylamino or thioalkyl;

each of $R_{11}$, $R_{12}$, $R_{13}$ and $R_{14}$, are independently hydrogen, halogen, oxo, thio, perhaloalkyl, perhaloalkoxy, hydroxy, thiol or $(C_1-C_3)$alkyl; and one of $R_5$ and $R_{10}$ is a halogen and the other is hydrogen; to provide the compound of formula I.

4. The method of claim 3, further comprising converting a racemic compound of formula I into substantially pure optically active form; converting one compound of formula I into another; removing a protecting group; forming a pharmaceutically acceptable salt or prodrug thereof; or a combination thereof; to obtain a different compound of formula I.

5. The method of claim 3 wherein said Pd(0) or Pd(II) catalyst is tetrakis triphenylphosphine palladium or (bis-tri-o-tolylphosphine)palladium and said cyclization is carried out in the presence of a base.

6. The method of claim 3 wherein said cyclization is carried out in the presence of a base.

7. A pharmaceutical composition comprising at least one compound of claim 1 and a pharmaceutically acceptable excipient or diluent.

8. The compound of claim 1 wherein at least one of the elements of the compound of formula I is a radiolabeled element.

9. A diagnostic tool for modulating 5-HT receptor function comprising the radiolabeled compound of claim 8.

10. The compound of claim 8 wherein the radiolabeled element is one or more of $^2H$, $^3H$, $^{11}C$, $^{13}C$, $^{14}C$, $^{13}N$, $^{15}N$, $^{15}O$, $^{18}F$, $^{99m}Tc$, $^{31}P$, S, $^{123}I$ and $^{125}I$.

* * * * *